United States Patent [19]

Ferland et al.

[11] 4,033,974

[45] July 5, 1977

[54] PYRIDYLMETHYL ESTERS OF N-(PHENOXYALKANOYL)PEPTIDE DERIVATIVES

[75] Inventors: Jean-Marie Ferland, St. Laurent; Amedeo Failli, Montreal; Hans U. Immer, Mount Royal; Manfred K. Gotz, Hudson, all of Canada

[73] Assignee: American Home Products Corporation, New York, N.Y.

[22] Filed: Feb. 11, 1976

[21] Appl. No.: 657,118

Related U.S. Application Data

[62] Division of Ser. No. 505,103, Sept. 11, 1974, Pat. No. 3,956,484.

[52] U.S. Cl. ............... 260/295.5 R; 260/295.5 A; 424/263

[51] Int. Cl.² ..................................... C07D 213/55
[58] Field of Search ............ 260/295.5 A, 295.5 R

[56] References Cited

OTHER PUBLICATIONS

Ugi, "Isonitrile Chemistry," Academic Press, pp. 145–149 (1971).

*Primary Examiner*—Alan L. Rotman

[57] ABSTRACT

Pyridylmethyl esters of N-(phenoxyalkanoyl)peptide derivatives are disclosed. The derivatives are characterized by having a phenoxyalkanoyl group and a pyridylmethyloxy group-joined together by a peptide group. They possess antihyperlipoproteinemic activity. In addition, methods for their preparation and use are disclosed.

6 Claims, No Drawings

PYRIDYLMETHYL ESTERS OF N-(PHENOXYALKANOYL)PEPTIDE DERIVATIVES

This is a division of application Ser. No. 505,103, filed Sept. 11, 1974 and now U.S. Pat. No. 3,956,484.

BACKGROUND OF THE INVENTION a. Field of the Invention

This invention relates to pyridylmethyl esters of N-(phenoxyalkanoyl)peptides having valuable pharmaceutical properties, to intermediates for preparing the pyridylmethyl esters, to processes for preparing said esters and intermediates, and to a method for using the pyridylmethyl esters.

b. Prior Art

The association of excessive plasma concentrations of lipoproteins or of plasma lipids with increased risk of heart attack, stroke, and sudden death is well established. Consequently, the consensus of informed opinion is that elevated levels of cholesterol and/or triglycerides should be reduced by appropriate longterm therapy.

The generally accepted Frederickson-Levy-Lees classification of lipid disorders based on lipoprotein disturbances lists five categories, Types I to V, of hyperlipoproteinemia. This classification allows a more rational choice of therapeutic programs for the treatment of hyperlipoproteinemia, see R. I. Levy, Fed. Proc. 30, 829 (1971). Although a vsriety of drugs are available for the treatment of hyperlipoproteinemia, none of them are suitable for the general treatment of the disease. Thus, at the present time, the preferred drugs for treating the disease are dependent on the classification of the lipid disorder and are different for each class; for example, see R. S. Lees and D. E. Wilson, New. Engl. J. Med., 284, 186 (1971).

The pyridylmethyl esters of this invention have been found now to be effective for reducing levels of cholesterol and triglycerides in the blood of warm blooded animals suffering from hyperlipoproteinemia and associated conditions. The pyridylmethyl esters are effective at dosages which do not elicit undesirable side effects. Furthermore, the esters are effective for treating a broad sector of the population suffering from the disease and find use for the treatment of Types II, III, IV and V hyperlipoproteinemia in general.

The pyridylmethyl esters of this invention are prepared by a convenient process from readily available starting materials. Consequently, the esters are inexpensive and readily available.

The pyridylmethyl esters of this invention feature a new combination of three chemical subunits; namely, a phenoxyalkanoyl group and a pyridylmethyloxy group joined together by a peptide group. Related prior art compounds include 3-pyridylmethyl esters of phenoxyalkanoic acid, U.S. Pat. No. 3,369,025, issued Feb. 13, 1968 and N-(carboxyalkyl)-phenoxyalkanoic acid amides, U.S. Pat. No. 3,364,249, issued Jan. 16, 1968. The prior art compounds are distinguished from the compound of the present invention in that they contain only two of the aforementioned subunits.

SUMMARY OF THE INVENTION

The pyridylmethyl esters of this invention are represented by formula 1,

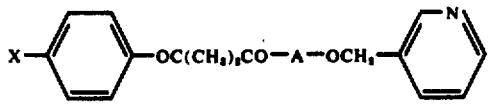

in which X is selected from the group consisting of bromine, chlorine, and lower alkyl and A is selected from the group consisting of the amino acid radicals $NHCH_2CO$, $NHCH_2CONHCH_2CO$ and

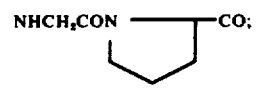

and acid addition salts thereof with pharmaceutically acceptable acids.

The compounds of formula 1 and the acid addition salts thereof possess hypocholesterolemic and triglyceride lowering properties and are useful as antihyperlipoproteinemic agents for the treatment of hyperlipoproteinemia and associated conditions. The compounds are prepared readily by processes disclosed herein.

DETAILS OF THE INVENTION

The term "hyperlipoproteinemia" as used herein contemplates an increase in one or more of the plasma lipoprotein classes and includes conditions wherein the levels of plasma cholesterol, triglycerides or both are increased.

The term "lower alkyl" as used herein contemplates hydrocarbon radicals having one to three carbon atoms and includes methyl, ethyl, isopropyl and propyl.

The acid addition salts are prepared by reacting the corresponding base form of the compound of formula 1 with substantially one equivalent or preferably with an excess of the appropriate acid in an organic solvent, for example, ether or an ethanol ether mixture. These salts, when administered to warm blooded animals possess the same pharmacologic activities as the corresponding bases. For many purposes it is convenient to administer the salts rather than the base compounds. Among the acid addition salts suitable for this purpose are salts such as the sulfate, phosphate, lactate, tartrate, maleate, citrate, hydrobromide and hydrochloride. Both the base compounds and the salts have the distinct advantage of possessing a relatively low order of toxicity.

The term "activated ester" as used herein contemplates carboxyl-activating groups employed in peptide chemistry to promote facile condensation of a carboxyl group with a free amino group of an amino acid derivative. Descriptions of these carboxyl-activating groups are found in general textbooks of peptide chemistry; for example, K. D. Kopple, "Peptides and Amino Acids," W. A. Benjamin, Inc., New York, 1966, pp. 50–51 and E. Schroder and K. Lubke, "The Peptides"; Vol. 1, Academic Press, New york, 1965, pp. 77–128. The following carboxyl-activating groups have proved to be particularly suitable in the processes of this invention: 2,4,5-trichlorophenyl, pentachlorophenyl, p-nitrophenyl, succinimido and 1-benzotriazolyl.

The hypocholesterolemic and triglyceride lowering properties of the compounds of formula 1 of the present invention are demonstrated in standard pharmacologic tests, for example, in procedures similar to the in vivo tests described by C. H. Duncan and M. M. Best, Amer. J. Clin. Nutr., 10, 297 (1962), and by the general tests described by L. W. Kinsell in "Pharmacologic Techniques in Drug Evaluation," Vol. 2, P. E. Siegler and J. H. Moyer, Eds., Year Book Medical Publishers, Inc., Chicago, 1967, pp. 711–720.

When used as antihyperlipoproteinemic agents, a blood cholesterol and triglyceride lowering amount of the compounds of formula 1 is administered to hyperlipoproteinemic, warm blooded animals, for example rats, either alone or with pharmaceutically acceptable carriers, the proportion of such carriers being determined by the solubility and chemical nature of the compound, chosen route of administration and standard biological practice. For example, the compounds may be administered orally in solid form containing such excipients as starch, milk sugar, certain types of clay and so forth. They may also be administered orally in the form of solutions or they may be injected parenterally. For parenteral administration they may be used in the form of a sterile solution containing other solutes, for example, enough saline or glucose to make the solution isotonic.

The dosage of the present pyridylmethyl esters will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects and preferably at a level that is in a range of from about 0.1 mg to about 100 mg per kilo per day, although as aforementioned variations will occur. However, a dosage level that is in the range of from about 1.0 mg to about 50 mg per kilo per day is most desirably employed in order to achieve effective results.

PROCESSES

The following is a schematic representation of the process for preparing the pyridylmethyl esters of formula 1

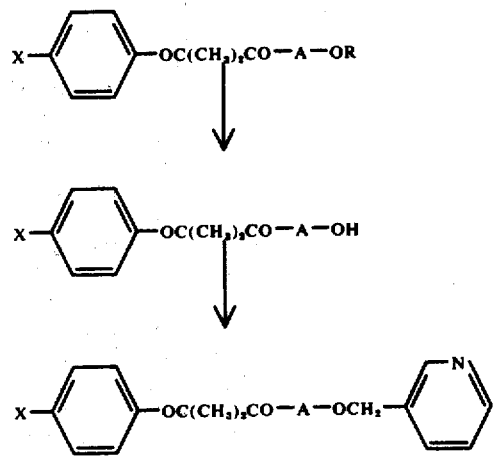

wherein X and A are as defined herein and R is lower alkyl.

More specifically, the compound of formula 1 is conveniently prepared by esterification of the corresponding acid of formula 3 in which X and A are as defined in the first instance with 3-pyridinemethanol. Although a variety of esterification methods are applicable, a convenient and effective method involves reacting the appropriate corresponding acid of formula 3 with substantially an equivalent amount of 3-pyridinemethanol in the presence of substantially one equivalent of dicyclohexylcarbodiimide (DCC) in the presence of an inert organic solvent, for example, ethyl acetate, tetrahydrofuran or chloroform. Reaction times and temperatures are not critical for this reaction and can vary from two or three hours to three or four days at 0° to 100° C. A convenient choice of time and temperature includes 24 to 72 hours at 20° to 40° C. Thereafter the precipitate; urea derivative is removed from the reaction and the solvent evaporated to give the desired pyridylmethyl ester.

Alternatively, the desired pyridylmethyl ester of formula 1 is obtained by reacting said corresponding acid of formula 3 with an excess of thionyl chloride to obtain the corresponding acid chloride of the said acid of formula 3, followed by condensing the acid chloride with 3-pyridinemethanol using pyridine as a reaction medium. The reaction times and temperatures of previous method, i.e. preferably 24 to 72 hours at 20° to 40° C, are suitable for effecting the condensation.

The said corresponding acid of formula 3 wherein X and A are as defined in the first instance is known, for example N-[2-(p-chlorophenoxy)-2-methylpropionyl]glycine, see U.S. Pat. No. 3,364,249, cited above, or the acid is obtained by hydrolyzing the corresponding ester of formula 2 in which X, A and R are as defined in the first instance. Preferred hydrolyzing conditions involve subjecting the ester of formula 2 to the action of a base, for example, sodium or potassium hydroxide, in the presence of sufficient water to effect hydrolysis of the ester. The hydrolysis is performed in an inert organic solvent, for example, methanol, ethanol or methoxyethanol. Under these conditions the hydrolysis is completed usually within 15 to 180 minutes at −10° to 50° C, preferably 0° C.

The requisite corresponding ester of formula 2 is either known, for example, N-[2-(p-chlorophenoxy)-2-methylpropionyl]glycine ethyl ester, see U.S. Pat. No. 3,364,249, cited above, or is prepared by known methods.

A convenient process for preparing the requisite ester of formula 2 in which X and R are as defined herein and A is NHCH$_2$CO comprises condensing the "activated ester" of the appropriate phenoxyalkanoic acid of formula X—⌬—OC(CH$_3$)$_x$COOH wherein X is as defined herein, see U.S. Pat. No. 3,262,850, issued July 26, 1966, with a lower alkyl ester of glycine, preferably methyl glycinate or ethyl glycinate.

Similarly, a convenient process for preparing the requisite ester of formula 2 in which X and R are as defined herein and A is NHCH$_2$CONHCH$_2$CO comprises condensing said "activated ester" of the phenoxyalkanoic acid of formula

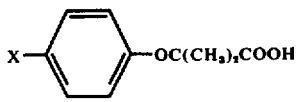

with a lower alkyl ester of glycylglycine, preferably the methyl or ethyl ester; for example, see H. N. Rydon and P. W. G. Smith, J. Chem. Soc., 2542 (1955).

Another convenient process for preparing the requisite ester of formula 2 in which X and R are as defined herein and A is $NHCH_2-CONHCH_2CO$ comprises condensing the "activated ester" of the aforementioned acid of formula 3 wherein X is as defined herein and A is $NHCH_2CO$ with a lower alkyl ester of glycine.

Still another convenient process for preparing the requisite ester of formula 2 in which X and R are as defined herein and A is $NHCH_2CONHCH_2CO$ comprises reacting said phenoxyalkanoic acid of formula

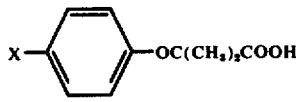

with formaldehyde, a base selected from the group consisting of ammonia and ammonium hydroxide, and a lower alkyl isocyanoacatate, preferably ethyl isocyanoacetate [R. Appel, et al., Angew. Chem., Int. ed., 10, 132 (1971)] in a four-component condensation, see P. Hoffmann, et al., in "Isonitrile Chemistry," [Organic Chemistry, Vol. 20, I. Ugi, Ed., Academic Press, New York, 1971, p. 145].

Although not critical it is preferably to use approximately one to two molar equivalents of said acid and ammonia or ammonia hydroxide to one equivalent of the other two components. The condensation is effected most conveniently in an inert solvent, for example, halogenated hydrocarbons including methylene dichloride, chloroform, and carbon tetrachloride, ethers and cyclic ethers including dioxane, diethyl ether and tetrahydrofuran, or lower aliphatic alcohols including methanol, ethanol and propanol. However, when the four starting materials are mutually soluble or the mixture thereof becomes liquid during the course of the condensation the solvent may be omitted without any deleterious effects.

The temperature and duration of the condensation also are not critical. The reaction may be performed at temperatures ranging from −20° to 100° C.; however, a range from 0° to 40° C is most convenient. The reaction time varies widely and depends on the reactivity of the various starting materials; however, reaction times from 15 minutes to several days are employed generally, with six hours to four days being preferred.

Thereafter the desired ester of formula 2 is isolated and purified according to standard procedures. For instance the product is extracted with a water-immiscible solvent and, if needed, purified by chromatography and crystallization.

A convenient process for preparing the requisite ester of formula 2 in which X and R are as defined herein and A is

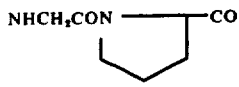

comprises condensing an "activated ester" of the aforementioned corresponding acid of formula 3 in which X is as defined herein and A is $NHCH_2CO$ with a lower alkyl ester of proline, for example, proline methyl ester, to obtain the requisite ester directly.

The following examples illustrate further this invention.

EXAMPLE 1

N-{N-[2-(p-Chlorophenoxy)-2-methylpropionyl]glycyl}-L-proline methyl ester (2, X = Cl,

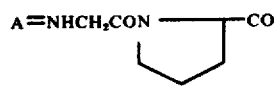

and R = $CH_3$)

To a mixture of proline methyl ester hydrochloride (15.9 g) and triethylamine (17.3 ml) in dimethylformamide (160 ml) and tetrahydrofuran (672 ml) at 0° C, a solution of the "activated ester", N-{N-[2-(p-chlorophenoxy)-2-methylpropionyl]glycine} succinimido ester (45.0 g) in dimethylformamide (160 ml) is added. The suspension is stirred at room temperature for 18 hr, evaporated to ½ of its initial volume under reduced pressure, poured into ice-cold water (2 liters) and stirred at 0° C for 1 hr. The mixture is extracted with ethyl acetate. The organic extract is washed and evaporated. The crude product obtained is filtered through silica gel using 20% acetone/ethyl acetate as solvent. Evaporation of the filtrate gives the title product nmr (CDCl$_3$) δ 1.5 (s, 6H), 3.73 (s, 3H), 6.9 and 7.25 (d, J = 8.5, 4H).

The above activated ester is obtained as follows:

To a solution of N-[2-(p-chlorophenoxy)-2-methylpropionyl]-glycine (28 g), prepared in Example 2, in dioxane (250 ml) is added a solution of N-hydroxysuccinimide (11.8 g) in dioxane (300 ml). To the cooled solution (12° C) is added a solution of DCC (21.2 g) in dioxane (150 ml). The mixture is stirred at 12° C for 2 hr and at room temperature for 18 hr. The solid is collected on a filter and washed with dioxane. The filtrate is evaporated to give the activated ester, N-{N-[2-(p-chlorophenoxy)-2-methylpropionyl]glycine} succinimido ester.

By following the procedure of Example 1 but replacing proline methyl ester hydrochloride with glycine ethyl ester hydrochloride, N-{N-[2-(p-chlorophenoxy)-2-methylpropionyl]glycyl}glycine ethyl ester, m.p. 83°–84° C (after recrystallization from ether-hexane), is obtained.

Likewise, by following the procedure of Example 1 but replacing proline methyl ester hydrochloride with glycylglycine ethyl ester and replacing the "activated ester" N-{N-[2-(p-chlorophenoxy)-2-methylpropionyl]glycine} succinimido ester with an equivalent amount of the "activated ester", 2-(p-chlorophenoxy)-2-methylpropionic acid succinimido ether, obtained in an analogous manner as the aforementioned "activated ester", N-{N-[2-(p-chlorophenoxy)-2-metylpropionyl]glycyl}glycine ethyl ester again is obtained.

EXAMPLE 2

N-[2-(p-Chlorophenoxy)-2-methylpropionyl]glycine
(3, X = Cl and A = NHCH₂CO)

To a stirred solution of the ester of formula 2, N-[2-(p-chlorophenoxy)-2-methylpropionyl]glycine methyl ester (9.5 g), in redistilled methanol (83 ml) cooled at 0° C, IN NaOH (44.5 ml) is added. The mixture is stirred at room temperature for 30 minutes and then most of the solvent is removed under reduced pressure at 25° C. The residue is diluted with brine (300 ml). The mixture is cooled to 0° C and acidified with IN HCL to pH 2. After stirring an additional 30 minutes in the cold, the precipitate is collected, washed to neutrality with cold water and dried to yield the title compound, mp 112°–113° C, nmr (CDCl₃) δ 1.5 (s, 6H), 6.9 and 7.25 (d, J = 9.0, 4H), 7.7 (1H), 9.45 (1H).

In the same manner but replacing the above ester of formula 2 with an equivalent amount of N-{N-[2-(p-chlorophenoxy)2-metylpropionyl]glycyl}glycine ethyl ester, N-{N-[2-(p-chlorophenoxy)-2-methylpropionyl]glycyl}glycine, nmr (CDCl₃) δ 1.45 (s, 6H), 4.1 (d, J = 4.5, 4H), 7.15 (m, 4H), 9.4 (s, 1H), is obtained.

In the same manner but replacing the above ester of formula 3 with an equivalent amount of N-{N-[2-(p-chlorophenoxy)-2-methylpropionyl]glycyl}-L-proline, methyl ester, described in Example 1, N-{N-[2-(p-chlorophenoxy)-2-methylpropionyl]glycyl}-L-proline, mp 144°–145° C after recrystallization from acetoneether, is obtained.

By following the procedure of Example 2 and using the appropriate ester of formula 2, other corresponding acids of formula 3 are obtained. More particularly exemplified, the use of N-[2-(p-methylphenoxy)-2-methylpropionyl]glycine ethyl ester affords N-[2-(p-methylphenoxy)-2-methylpropionyl]glycine.

Likewise, N-{N-[2-(p-bromophenoxy)-2-methylpropionyl]-glycyl}-L-proline methyl ester affords N-{N-[2-(p-bromophenoxy)-2-methylpropionyl]glycyl}-L-proline.

Likewise, N-{N-[2-(p-methylphenoxy)-2-methylpropionyl]-glycyl}glycine methyl ester affords N-{N-[2-(p-methylphenoxy)-2-methylpropionyl glycyl}glycine.

EXAMPLE 3

N-[2-(p-Chlorophenoxy)-2-methylpropionyl]glycine 3-pyridylmethyl ester (1, X = Cl and A - NHCH₂CO)

To a solution of the acid of formula 3, N-[2-(p-chlorophenoxy)-2-methylpropionyl]glycine (17.5 g), described in Example 2, and 3-pyridinemethanol (9.08 g) in ethyl acetate (400 ml), a solution of DCC (13.7 g) in ethyl acetate (400 ml) is added dropwise. The suspension is stirred at room temperature for 64 hr. The resulting precipitate is collected on a filter, and washed with ethyl acetate. The combined filtrate and washings are evaporated to dryness. The residue is subjected to chromatography on silica gel using 20% acetone in ethyl acetate as the eluant. Evaporation of the eluate and crystallization of the resulting residue from benzene-petroleum ether (40°–60° C) gives the title compound, mp 67°–69° C, nmr, (CDCl₃) δ 1.48 (s, 6H), 4.15 (d, J = 5.5, 3H), 5.2 (2H), 6.8–7.85 (m, 8H), 8.56 (1H).

In the same manner but replacing the above acid of formula 3 with an equivalent amount of N-{N-[2-(p-chlorophenoxy)-2-methionyl]glycyl}glycine, described in Example 2, N-{N-[2-(p-chlorophenoxy)-2-methylpropionyl]glycyl}glycine 3-pyridylmethyl ester, mp 129°–130° C (recrystallized from ethyl acetate-hexane), nmr (CDCl₃) δ 1.5 (s, 6H), 4.1 (m, 4H), 5.25 (s, 2H), 7.3 (m, 8H), is obtained.

In the same manner but replacing the above acid of formula 3 with an equivalent amount of N-{N-[2-(p-chlorophenoxy)2-methylpropionyl]glycyl}-L-proline, described in Example 2, N-{N-[2-(p-chlorophenoxy)-2-methylpropionyl]glycyl}-L-proline 3-pyridylmethyl ester, nmr (CDCl₃) δ 1.52 (6H), 4.11 (D, J = 5.5, 2H), 5.22 (2H), 7.1 and 7.65 (8H), 8.4 (1H), M⁺ = 459, is obtained.

By following the procedure of Example 3 and using the appropriate acid of formula 3, other pyridyl esters of formula 1 are obtained.

More particularly exemplified, the use of N-[2-(p-methylphenoxy)-2-methylpropionyl]glycine, described in Example 2, affords N-[2-(p-methylphenoxy)-2-methylpropionyl]glycine 3-pyridylmethyl ester.

Likewise, N-{N-[2(p-bromophenoxy)-2-methylpropionyl]-glycyl}-L-proline, described in Example 2, affords N-{N-[2-(p-bromophenoxy)-2-methylpropionyl]glycyl}-L-proline 3-pyridylmethyl ester.

Likewise, N-{N-[2-(p-methylphenoxy)-2-methylpropionyl]-glycyl}glycine, described in Example 2, gives N-{N-[2-(p-methylphenoxy)2-methylpropionyl]-glycyl}glycine 3-pyridinylmethyl ester.

EXAMPLE 4

N- N-[2-(p-Chlorophenoxy)-2-methylpropionyl]-glycyl glycine ethyl ester (2, X = Cl, A = NHCH₂CONHCH₂CO and R = C₂H₅)

To a stirred solution of 2-(p-chlorophenoxy)-2-methylpropionic acid (2.58 g), in methanol (12 ml) at 0°–10° C is added aqueous ammonium hydroxide (3.6 N, 3.33 ml) followed by formaldehyde (36% solution in water, 0.72 ml) and ethyl isocyanoacetate (redistilled, 0.677 g). The mixture is stirred for 60 minutes in the cold and then for 3 days at room temperature. The pale yellow solution is evaporated to dryness and the residue (thick yellow oil) is dissolved in chloroform (100 ml). The solution is washed with 5% sodium bicarbonate (2 × 10 ml) and brine to neutrality. The organic layer is dried MgSO₄), filtered and the filtrate evaporated to dryness under reduced pressure to give a yellow oil. The yellow oil is subjected to chromatography on silica gel (320 g). Elution with benzene-ethyl acetate (1:1) affords first a less polar oil followed by the more polar yellow oil. The more polar yellow oil crystallizes on trituration with hexane. Recrystallization of the latter from ether-hexane gives the title compound, m.p. 82°–83° C, identical to the compound of the same name described in Example 1.

We claim:

1. A compound of the formula

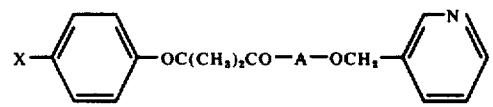

in which X is selected from the group consisting of bromine, chlorine and lower alkyl and A is selected from the group consisting of NHCH₂CO, NHCH₂CONHCH₂CO and

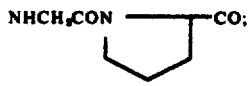

and acid addition salts thereof with pharmaceutically acceptable acids.

2. N-[2-(p-Chlorophenoxy)-2-methylpropionyl]glycine 3-pyridylmethyl ester, as claimed in claim 1.

3. N-{N-[2-(p-Chlorophenoxy)-2-methylpropionyl]glycyl}-glycine 3-pyridylmethyl ester, as claimed in claim 1.

4. N-{N-[2-(p-Chlorophenoxy)-2-methylpropionyl]glycyl}-L-proline 3-pyridylmethyl ester, as claimed in claim 1.

5. N-{N-[2-(p-(Chlorophenoxy)-2-methylpropionyl]-glycyl}-L-proline and its corresponding methyl ester.

6. N-{N-[2-(p-Chlorophenoxy)-2-methylpropionyl]-glycyl}glycine and its corresponding ethyl ester.

* * * * *